US007186276B2

(12) United States Patent  (10) Patent No.: US 7,186,276 B2
Lagrange  (45) Date of Patent: Mar. 6, 2007

(54) DYE COMPOSITION COMPRISING AT LEAST ONE DIRECT DYE, DYEING PROCESSES, USES AND MULTI-COMPARTMENT DEVICES

(75) Inventor: Alain Lagrange, Coupvray (FR)

(73) Assignee: L'Oreal, Paris (FR)

( * ) Notice: Subject to any disclaimer, the term of this patent is extended or adjusted under 35 U.S.C. 154(b) by 410 days.

(21) Appl. No.: 10/742,800

(22) Filed: Dec. 23, 2003

(65) Prior Publication Data

US 2004/0194228 A1 Oct. 7, 2004

Related U.S. Application Data

(60) Provisional application No. 60/468,631, filed on May 8, 2003.

(30) Foreign Application Priority Data

Dec. 23, 2002 (FR) .................................. 02 16568

(51) Int. Cl.
*A61K 7/13* (2006.01)
(52) U.S. Cl. ....................... 8/405; 8/406; 8/407; 8/410; 8/411; 8/423; 8/426; 8/437; 8/562; 8/565; 8/566; 8/568; 8/570; 8/571; 8/572; 8/573; 8/574; 8/575; 8/576; 8/579; 549/200; 546/146; 552/100; 540/122
(58) Field of Classification Search ............... 8/405, 8/406, 407, 410, 411, 423, 426, 437, 562, 8/565, 566, 568, 570, 571, 572, 573, 574, 8/575, 576, 579; 549/200; 546/146; 552/100; 540/122
See application file for complete search history.

(56) References Cited

U.S. PATENT DOCUMENTS

| | | | |
|---|---|---|---|
| 2,528,378 A | 10/1950 | Mannheimer et al. | |
| 2,781,354 A | 2/1957 | Mannheimer et al. | |
| 2,798,053 A | 7/1957 | Brown | |
| 2,923,692 A | 2/1960 | Ackerman et al. | |
| 3,578,387 A | 5/1971 | Zviak etal. | |
| 3,915,921 A | 10/1975 | Schlatzer | |
| 4,003,699 A | 1/1977 | Rose et al. | |
| RE30,199 E | 1/1980 | Rose et al. | |
| 4,237,243 A | 12/1980 | Quack et al. | |
| 4,509,949 A | 4/1985 | Huang et al. | |
| 4,557,732 A * | 12/1985 | Hahnke et al. ................ 8/538 |
| 4,670,546 A | 6/1987 | Doré et al. ................ 534/612 |
| 4,823,985 A | 4/1989 | Grollier et al. | |
| 5,061,289 A | 10/1991 | Clausen et al. | |
| 5,380,340 A | 1/1995 | Neunhoeffer et al. | |
| 5,708,151 A | 1/1998 | Möckli | |
| 5,766,576 A | 6/1998 | Lowe et al. | |
| 5,980,587 A | 11/1999 | Samain | |
| 6,099,592 A | 8/2000 | Vidal et al. | |
| 6,099,593 A | 8/2000 | Terranova et al. | |
| 6,338,741 B1 | 1/2002 | Vidal et al. | |
| 6,468,316 B1 | 10/2002 | Genet et al. | |
| 6,554,872 B2 | 4/2003 | Genet et al. | |
| 6,828,443 B1 | 12/2004 | Hollenberg et al. | |
| 2001/0001333 A1 | 5/2001 | Samain | |
| 2001/0049848 A1 | 12/2001 | Genet et al. ................... 8/405 |
| 2001/0049849 A1 | 12/2001 | de la Mettrie et al. | |
| 2002/0050013 A1 | 5/2002 | Vidal et al. | |
| 2004/0074016 A1 | 4/2004 | Genet et al. | |
| 2005/0039268 A1 | 2/2005 | Plos et al. | |

FOREIGN PATENT DOCUMENTS

| | | |
|---|---|---|
| DE | 23 59 399 | 6/1975 |
| DE | 33 13 965 | 10/1983 |
| DE | 38 43 892 A1 | 6/1990 |
| DE | 41 33 957 A1 | 4/1993 |
| DE | 195 43 988 A1 | 5/1997 |
| DE | 198 02 940 | 8/1999 |
| EP | 0 216 479 B1 | 4/1987 |
| EP | 0 714 954 B1 | 6/1996 |
| EP | 0 770 375 B1 | 5/1997 |
| FR | 1 584 965 | 1/1970 |
| FR | 2 416 723 | 9/1979 |
| FR | 2 586 913 | 3/1987 |
| FR | 2 733 749 | 11/1996 |
| FR | 2 741 798 | 6/1997 |

(Continued)

OTHER PUBLICATIONS

English language Derwent Abstract of DE 198 02 940, Aug. 5, 1999.
English language Derwent Abstract of FR 2 822 696, Oct. 4, 2002.
"Encyclopedia of Chemical Technology", Kirk-Othmeer, Third Edition, 1982, vol. 3, pp. 896-900 & vol. 15, pp. 439-458.
"Polymers in Nature", by E.A. MacGregor & C.T. Greenwood, published by John Wiley & Sons, Chapter 6, pp. 240-328, 1980.
"Handbook of Surfactants", by M.R. Porter, published by Blackie & Sons (Glasgow and London), 1991, pp. 116-178.

(Continued)

*Primary Examiner*—Eisa Elhilo
(74) *Attorney, Agent, or Firm*—Finnegan, Henderson, Farabow, Garrett & Dunner, L.L.P.

(57) ABSTRACT

Disclosed herein is a dye composition for dyeing human keratin fibers, such as the hair, comprising a direct polycationic dye of formula (I) below:

$$\text{Col-Z-Col} \tag{I}$$

in which

Col, which may be identical or different, is a monocationic dye chosen from azo dyes, methine dyes, azomethine dyes, and phenothiazine dyes; and Z is chosen from linear and branched, saturated and unsaturated C1–C20 hydrocarbon-based groups comprising at least one nitrogen atom and bearing at least two cationic charges, and also to processes for dyeing human keratin fibers using said composition, to the use of the dyes of formula (I) as direct dyes, and to multi-compartment devices.

44 Claims, No Drawings

FOREIGN PATENT DOCUMENTS

| | | |
|---|---|---|
| FR | 2 750 048 | 12/1997 |
| FR | 2 786 481 | 6/2000 |
| FR | 2 788 220 A1 | 7/2000 |
| FR | 2 822 696 | 10/2002 |
| GB | 1 026 978 | 4/1966 |
| GB | 1 153 196 | 5/1969 |
| JP | 555-22638 | 2/1980 |
| JP | 2-19576 | 1/1990 |
| JP | 5-163124 | 6/1993 |
| JP | 2000-204026 | 7/2000 |
| JP | 2000-230131 | 8/2000 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 01/02492 | 1/2001 |
| WO | WO 01/66646 | 9/2001 |
| WO | WO 02/100365 A1 | 12/2002 |

OTHER PUBLICATIONS

French Search Report for FR 02 16568 (the Prority Application for U.S. Application No. 10/742,800), dated Sep. 12, 2003, Examiner S. Werner.
English language Derwent Abstract of EP 0 770 375 B1.
English language Derwent Abstract of JP 55-22638.
English language Derwent Abstract of JP 2-169571.
English language Derwent Abstract of JP 5-163124.

* cited by examiner

DYE COMPOSITION COMPRISING AT LEAST ONE DIRECT DYE, DYEING PROCESSES, USES AND MULTI-COMPARTMENT DEVICES

This application claims benefit of U.S. Provisional Application No. 60/468,631, filed May 8, 2003.

Disclosed herein is a dye composition for dyeing human keratin fibers, such as the hair, comprising at least one direct polycationic dye, processes for dyeing human keratin fibers using the composition comprising a direct polycationic dye, and their use and to multi-compartment devices.

It is well-known practice to dye human keratin fibers, such as the hair, with dye compositions comprising oxidation dye precursors, which are generally known as oxidation bases. These oxidation bases may be colorless or weakly colored compounds, that, when combined with oxidizing products, may give rise to colored compounds by a process of oxidative condensation.

It is also well-known that the shades obtained with these oxidation bases may be varied by combining them with couplers or coloration modifiers. The variety of molecules used as oxidation bases and couplers may allow a wide range of colors to be obtained.

This oxidation dyeing process comprises applying to keratin fibers at least one of oxidation base and/or mixtures of oxidation bases and couplers with an oxidizing agent, for example aqueous hydrogen peroxide solution, leaving the agents on the fibers, and then rinsing the fibers. The colorations resulting therefrom may be permanent, strong, and resistant to external agents, such as, light, weather, washing, perspiration, and rubbing. This process, which may be applied at basic pH, may make it possible to dye and lighten the fibers simultaneously, which may be reflected in practice by the possibility of obtaining a final coloration that is lighter than the original fiber color. In addition, lightening of the fibers may have the advantageous effect of generating a unified color in the case of grey hair, and of bringing out the color, i.e., making it more visible, in the case of naturally pigmented hair.

It is also well-known practice to dye human keratin fibers with a direct dye. The process conventionally used in direct dyeing comprises applying to the keratin fibers direct dyes, which may be colored and coloring molecules that have affinity for the fibers, leaving the dyes on the fibers, and then rinsing the fibers.

It is well-known practice, for example, to use nitrobenzene, anthraquinone, nitropyridine, azo, xanthene, acridine, azine, and triarylmethane direct dyes.

The colorations resulting therefrom may be, for example, chromatic colorations, but also may be temporary or semi-permanent because of the nature of the interactions linking the direct dyes to the keratin fiber. Desorption from the surface and/or core of the fiber may be responsible for the poor dyeing power and the poor fastness of these direct dyes with respect to washing or perspiration. These direct dyes may also be light-sensitive due to the poor resistance of the chromophore to photochemical attack, and which may lead over time to fading of the hair coloration. In addition, the light-sensitivity of these dyes may be dependent on their uniform distribution or their distribution as aggregates in the keratin fibers.

Further, it is well-known practice to use direct dyes in combination with oxidizing agents. However, the direct dyes may be sensitive to the action of oxidizing agents such as aqueous hydrogen peroxide solution, and reducing agents such as sodium bisulphite, which may make them difficult to use in lightening direct dyeing compositions based on aqueous hydrogen peroxide solution and based on a basifying agent, and in oxidation dye compositions in combination with precursors such as oxidation bases or couplers.

For example, it has been proposed in French Patent Application FR 1 584 965 and Japanese Patent Application JP 062 711 435 to dye the hair with dye compositions based on nitro direct dyes and/or dispersed azo dyes and an ammoniacal aqueous hydrogen peroxide solution, by applying to the hair a mixture of the dyes and of the oxidizing agent, prepared before use. However, the colorations obtained may have insufficient fastness, and disappear on shampooing, allowing the lightening of the hair fibers to show through. Such a coloration may become unattractive by changing over time.

It has also been proposed in Japanese Patent Applications JP 53 95693 and JP 55 022638 to dye hair with compositions based on cationic oxazine direct dyes and ammoniacal aqueous hydrogen peroxide solution, by applying to the hair an ammoniacal aqueous hydrogen peroxide solution in a first step, and then applying a composition based on the oxazine direct dye in a second step. This coloration may be unsatisfactory, due to the fact that it requires a process is slowed by the leave-in times of the two successive steps. If, moreover, an extemporaneous mixture of the oxazine direct dye with ammoniacal aqueous hydrogen peroxide solution is applied to the hair, either no coloration is obtained, or, a virtually non-existent coloration of the hair fiber may be obtained.

More recently, French Patent Application FR 2 741 798 describes dye compositions containing direct dyes comprising at least one of quaternized azo and azomethine nitrogen atoms, the compositions being extemporaneously mixed at basic pH with an oxidizing composition. These compositions may make it possible to obtain colorations with uniform, fast, and shiny glints. However, they may not allow keratin fibers to be dyed as strongly as with oxidation dye compositions.

There is thus a desire to find chromatic direct dyes that allow human keratin fibers to be dyed as strongly as oxidation dyes, which may also be just as light-fast as the oxidation dyes, and which may be resistant to weather, washing and perspiration. There is a desire for chromatic direct dyes that may be sufficiently stable in the presence of oxidizing and reducing agents to be able to obtain lightening of the fiber simultaneously either by using lightening direct compositions containing oxidation and/or reducing agents, or by using oxidation dye compositions based on oxidation dye precursors containing oxidation and/or reducing agents. There is also a desire to find direct dyes that may produce rises in color comparable to those obtained with oxidation dye precursors.

In addition, the present inventor sought to show one of more of the following characteristics: good harmlessness, little or no degradation of the keratin fibers and less selectivity compared with standard dyes.

At lease one of these aims may achieved with the embodiments disclosed herein, one of which is a composition for dyeing human keratin fibers, such as the hair, comprising, in a medium that is suitable for dyeing, at least one direct polycationic dye of formula (I) below:

$$\text{Col-Z-Col} \qquad (I)$$

in which

Col, which may be identical or different, represents a monocationic dye chosen from at least one of azo dyes, methine dyes, azomethine dyes, phenothiazine dyes, triarylmethane dyes, xanthene dyes, phenanthridine dyes, and phthalocyanin dyes; and Z is chosen from linear and branched, saturated and unsaturated C1–C20, such as C6–C18, hydrocarbon-based group comprising at least one nitrogen atom and bearing at least two cationic charges.

As used herein:

—the term "azo dye" means a molecule or a molecular residue that absorbs light radiation in the visible region, ranging from about 400 nm to about 750 nm, and comprises in its structure at least one sequence (A) not included in a ring

(A)

the term "methine dye" means a molecule or a molecular residue that absorbs light radiation in the visible region, ranging from about 400 nm to 750 nm, and comprises in its structure at least one sequence (B) not included in a ring

(B)

the term "azomethine dye" means a molecule or a molecular residue that absorbs light radiation in the visible region, ranging from about 400 nm to 750 nm, and comprises in its structure at least one sequence (C) not included in a ring

(C)

the term "triarylmethane dye" means a molecule or a molecular residue that absorbs light radiation in the visible region, ranging from about 400 nm to 750 nm, and comprises in its structure at least one sequence (D) wherein A is chosen from an oxygen

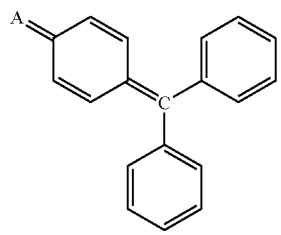
(D)

atom and a nitrogen atom;

—the term "xanthene dye" means a molecule or a molecular residue that absorbs light radiation in the visible region, ranging from about 400 nm to about 750 nm, and comprises in its structure at least one sequence (E)

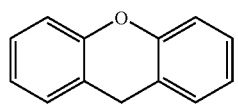
(E)

—the term "phenanthridine dye" means a molecule or a molecular residue that absorbs light radiation in the visible region, ranging from about 400 nm to about 750 nm, and comprises in its structure at least one sequence (F)

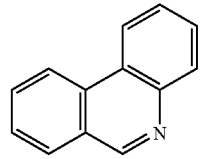
(F)

the term "phthalocyanin dye" means a molecule or a molecular residue that absorbs light radiation in the visible region, ranging from about 400 nm to about 750 nm, and comprises in its structure at least one sequence (G)

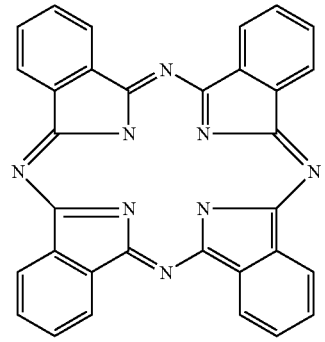
(G)

the term "phenothiazine dye" means a molecule or a molecular residue that absorbs light radiation in the visible region, ranging from about 400 nm to about 750 nm, and comprises in its structure at least one sequence (H)

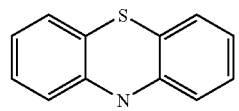
(H)

As used herein, the term "cationic charge," as it applies to Formula I only, means any quaternized nitrogen atom.

As used herein, the term "$C_1$–$C_{20}$ hydrocarbon-based group" means a $C_1$–$C_{20}$ such as $C_6$–$C_{18}$ aliphatic chain optionally interrupted with at least one, i.e., from 1 to 5, hetero atoms, for instance nitrogen, oxygen, sulphur, and phosphorus, this chain optionally comprising at least one, i.e., from 1 to 5, aromatic rings, at least one, i.e., from 1 to 5, aromatic or saturated heterocycles, at least one, i.e., from 1 to 5, aliphatic rings, optionally substituted with at least one, i.e., from 1 to 5, groups chosen from hydroxyl, carboxyl, ($C_1$–$C_4$)alkoxycarbonyl, hydrogenocarbonyl, $C_1$–$C_4$ alkoxy, $C_2$–$C_4$ acyl, amino, monoalkylamino, dialkylamino, mono($C_1$–$C_4$ hydroxyalkyl), di($C_1$–$C_4$ hydroxyalkyl), cyano, nitro, and sulphonato groups.

The chain may comprise at least one double bond and may comprise at least one triple bond. This hydrocarbon-based chain may also comprise at least one aromatic group such as benzene and naphthalene rings. The chain may also form at least one 3- to 6-membered carbon-based ring.

The attachment of the identical dye groups Col to the group Z may be performed directly on at least one of the cationic nitrogen atoms of the dyes, on at least one other atom of the dye molecule, or via at least one linker arm.

As disclosed herein, the structure of the group Z bearing at least two cationic charges may thus correspond to formula (II):

in which:

Z1 and Z3, which may be identical or different, represent a heterocycle bearing at least one hetero atom chosen from nitrogen, oxygen, sulphur, and phosphorus. These heterocyclic groups may be 5- to 8-membered and may optionally be fused with a benzene nucleus. They may be substituted with at least one of C1–C4 alkyl, carboxyl, C1–C4 alkoxy, (C1–C4)alkoxycarbonyl, hydroxyl, hydroxycarbonyl, amino, monoalkylamino, dialkylamino, mono(C1–C4 hydroxyalkyl)amino, di(C1–C4 hydroxyalkyl)amino, cyano, nitro, and sulphato groups.

For example, Z1 and Z3 may each bear a cationic charge.

$Z_2$ is a linear or branched hydrocarbon-based group containing from 0 to 10, such as from 2 to 6 carbon atoms.

For example, the heterocyclic group is chosen from isoimidazole, imidazole, pyridine, pyrazole, and pyrrole groups.

According to the present invention, the structure of the group Z may also correspond to formula (III):

in which:

n represents an integer from ranging from 1 to 10, such as from 2 to 5;

p represents an integer ranging from 1 to 10, such as from 2 to 5; and $Z_4$ represents a dicationic group containing from 2 to 16 carbon atoms, such as from 5 to 12 carbon atoms, this group being aliphatic; saturated or unsaturated; carbocyclic or polycarbocyclic, such as monocarbocyclic, bicarbocyclic, and tricarbocyclic; aromatic or polyaromatic, such as monoaromatic, biaromatic, and triaromatic; heterocyclic or polyheterocyclic, wherein the said heterocycles comprise from 1 to 5 hetero atoms chosen from at least one of nitrogen, sulphur, oxygen, and phosphorus, the group being optionally substituted with at least one group chosen from hydroxyls, carboxyls, $C_1$–$C_4$ alkoxycarbonyls, hydrogenocarbonyls, $C_1$–$C_4$ alkoxys, aminos, monoalkylaminos, dialkylaminos, $C_1$–$C_4$ monohydroxyalkyl, $C_1$–$C_4$ dihydroxyalkyl, cyanos, nitros, and sulphonatos.

For example, the group $Z_4$ may be chosen from diazoniabicyclooctanes and bipyridines.

In one embodiment, group Z of formula III comprises aliphatic groups Z, such as groups of the formula (IV)

in which n represents an integer ranging from 1 to 10, such as from 2 to 5;

m represents an integer ranging from 1 to 15, such as from 2 to 10;

p represents an integer ranging from 1 to 10, such as from 2 to 5; and $R_1$, $R_2$, $R_3$ and $R_4$, which may be identical or different, denote a $C_1$–$C_6$ alkyl radical.

According to one embodiment, the polycationic direct dyes disclosed herein may be at least one of azo, triarylmethane, phenanthrene, and methine dyes.

The compounds disclosed herein may include compounds that may be known per se.

Among the polycationic direct dyes disclosed herein that may be mentioned are the following compounds:

Compounds of formula (II):

N,N,N'',N''-tetramethyl-N,N''-bis{3-[4-[(3-methyl-2-(3H)-benzo-thiazolylidene)methyl]quinolinium-1-yl]butyl}-1,4-bipyridinium tetraiodide Compounds of formula (III)

[1,4-phenylenebis[methylene(dimethyliminio)-3,1-ethanediyl]]bis[2-({4-[(4-dimethylaminophenyl)(cyclohexa-2,5-dienylidene}-4-dimethylammonium)-methylene]phenyl}ethylamino)ethyl];

[1,4-phenylenebis[methylene(diethyliminio)-3,1-ethanediyl]]bis[2-({4-[(4-dimethylaminophenyl)(cyclohexa-2,5-dienylidene}-4-dimethylammonium)methylene]phenyl}ethylamino)ethyl];

1,3'-Bipyridinium 1',1'''-[1,4-phenylenebis[methylene(dimethyliminio)-3,1-propanediyl]]bis[1',2'-dihydro-6'-hydroxy-4'-methyl-5'-[[4-(phenylazo)phenyl]azo] tetrachloride;

1,3'-Bipyridinium 1',1'''-[(2-hydroxy-1,3-propanediyl)bis[(dimethyliminio)-3,1-propanediyl]]bis[1',2'-dihydro-6'-hydroxy-4'-methyl-2'-oxo-5'-[[4-(phenylazo)phenyl]azo] tetrachloride;

N,N-bis{3-[4-[(3-methyl-2(3H)-benzothiazolylidene)methyl]quinolinium-1-yl]propyl}-1,4-diazoniabicyclo[2,2,2]octane tetraiodide; and N N-bis{3-[4-[(3-methyl-2(3H)-benzothiazolylidene)methyl]quinolinium-1-yl]butyl}-1,4-diazoniabicyclo[2,2,2] octane tetraiodide;

Compounds of formula (IV)

Thiazolo[4,5-b]pyridinium 2,2'-[1,3-propanediylbis[(dimethyliminio)-3,1-propanediyl-1(4H)-quinolinyl-4-ylidenemethylidyne]]bis[6-bromo-4-methyl] tetraiodide;

Oxazolo[4,5-b]pyridinium 2,2'-[1,3-propanediylbis[(dimethyliminio)-3,1-propanediyl-1(4H)-quinolinyl-4-ylidenemethylidyne]]bis[4-methyl] tetraiodide;

Quinolinium 1,1'-[1,6-hexanediylbis[(dimethyliminio)-4,1-butanediyl]]bis[4-[(3-methyl-2(3H)-benzothiazolylidene)methyl] tetraiodide;

Quinolinium 1,1'-[1,6-hexanediylbis[(dimethyliminio)-3,1-propanediyl]]bis[4-[(3-methyl-2(3H)-benzothiazolylidene)methyl] tetraiodide;

Quinolinium 1,1'-[1,3-propanediylbis[(dimethyliminio)-4,1-butanediyl]]bis[4-[(3-ethyl-2(3H)-benzothiazolylidene)methyl] tetraiodide;

Quinolinium 1,1'-[1,3-propanediylbis[(dimethyliminio)-3,1-propanediyl]]bis[4-[(3-ethyl-2(3H)-benzothiazolylidene)methyl] tetraiodide;

Quinolinium 1,1'-[1,3-propanediylbis[(dimethyliminio)-5,1-pentanediyl]]bis[4-[(3-methyl-2(3H)-benzothiazolylidene)methyl] tetraiodide;

Quinolinium 4-[(3-methyl-2(3H)-benzothiazolylidene)methyl]-1-[3-[dimethyl[3-[dimethyl[4-4-[(3-methyl-2(3H)-benzothiazolylidene)methyl]quinolinio]butyl]ammonio]propyl]ammonio]propyl] tetraiodide;

Quinolinium 1,1'-[1,3-propanediylbis[(dimethyliminio)-2,1-ethanediyl]]bis[4-[(3-methyl-2(3H)-benzothiazolylidene)methyl] tetraiodide;

Benzothiazolium 2,2'-[1,3-propanediylbis[(dimethyliminio)-3,1-propanediyl-1(2H)-pyridinyl-2-ylidenemethylidyne]]bis[3-methyl] tetraiodide;

N,N,N''',N'''-tetramethyl-N,N''-bis{3-[4-[(3-methyl-2-(3H)-benzothiazolylidene)methyl]quinolinium-1-yl]butyl}-1,3-propanediammonium tetraiodide;

Naphtho[1,2-d]thiazolium 2,2'-[1,3-propanediylbis[(dimethyliminio)-3,1-propanediyl-1(4H)-quinolinyl-4-ylidenemethylidyne]]bis[1-methyl] tetraiodide;

8H-Naphth[2',1':4,5]oxazolo[3,2-a]azepinium 12,12'-[methylenebis-[(dimethyliminio)-3,1-propanediyl-1(4H)-quinolinyl-4-ylidene-2,1-ethanediylidene]]bis[9,10,11,12-tetrahydro-9-[3-(trimethylammonio)propyl];

Naphth[2',1':4,5]oxazolo[3,2-a]pyridinium 11,11'-[methylenebis[(dimethyliminio)-3,1-propanediyl-1(4H)-quinolinyl-4-ylidene-2,1-ethanediylidene]]bis[8,9,10,11-tetrahydro-8-[3-(trimethylammonio)propyl];

Naphth[2,1-d]oxazolium 2,2'-[methylenebis[(dimethyliminio)-3,1-propanediyl-1(4H)-quinolinyl-4-ylidene-1-propen-1-yl-3-ylidene]]bis[3-[3-(trimethylammonio)propyl];

8H-Naphtho[2',1':4,5]thiazolo[3,2-a]azepinium 12,12'-[methylenebis[(dimethyliminio)-3,1-propanediyl-1(4H)-quinolinyl-4-ylidene-2,1-ethanediylidene]]bis[9,10,11,12-tetrahydro-9-[3-(trimethylammonio)propyl];

Naphtho[2',1':4,5]thiazolo[3,2-a]pyridinium 11,11'-[methylenebis[(dimethyliminio)-3,1-propanediyl-1(4H)-quinolinyl-4-ylidene-2,1-ethanediylidene]]bis[8,9,10,11-tetrahydro-8-[3-(trimethylammonio)propyl];

Naphtho[2,1-d]thiazolium 2,2'-[methylenebis[(dimethyliminio)-3,1-propanediyl-1(4H)-quinolinyl-4-ylidene-1-propen-1-yl-3-ylidene]]bis[3-[3-(trimethylammonio)propyl];

Naphth[2',1':4,5]oxazolo[3,2-a]azocinium 13,13'-[methylenebis-[(dimethyliminio)-3,1-propanediyl-1(4H)-quinolinyl-4-ylidene-2,1-ethanediylidene]]bis[8,9,10,11,12,13-hexahydro];

Naphth[2',1':4,5]oxazolo[3,2-a]pyridinium 11,11'-[methylenebis-[(dimethyliminio)-3,1-propanediyl-1(4H)-quinolinyl-4-ylidene-2,1-ethanediylidene]]bis[8,9,10,11-tetrahydro];

8H-Naphtho[2,1-d]pyrrolo[2,1-b]oxazolium 10,10'-[methylenebis-[(dimethyliminio)-3,1-propanediyl-1(4H)-quinolinyl-4-ylidene-2,1-ethanediylidene]]bis[9,10-dihydro];

Naphtho[2',1':4,5]thiazolo[3,2-a]azocinium 13,13'-[methylenebis-[(dimethyliminio)-3,1-propanediyl-1(4H)-quinolinyl-4-ylidene-2,1-ethanediylidene]]bis[8,9,10,11,12,13-hexahydro];

Naphtho[2',1':4,5]thiazolo[3,2-a]pyridinium 11,11'-[methylenebis-[(dimethyliminio)-3,1-propanediyl-1(4H)-quinolinyl-4-ylidene-2,1-ethanediylidene]]bis[8,9,10,11-tetrahydro];

8H-Naphtho[2,1-d]pyrrolo[2,1-b]thiazolium 10,10'-[methylene-bis[(dimethyliminio)-3,1-propanediyl-1(4H)-quinolinyl-4-ylidene-2,1-ethanediylidene]]bis[9,10-dihydro];

Benzoxazolium 2,2'-[1,3-propanediylbis[(dimethyliminio)-3,1-propanediyl-1(4H)-pyridinyl-4-ylidenemethylidyne]]bis[3-methyl] tetraiodide;

Benzothiazolium 2,2'-[1,3-propanediylbis[(dimethyliminio)-3,1-propanediyl-1(4H)-pyridinyl-4-ylidene-1-propenyl-3-ylidene]]bis[3-methyl] tetraiodide;

Quinolinium 1,1'-[1,3-propanediylbis[(dimethyliminio)-3,1-propanediyl]]bis[4-[3-(3-methyl-2(3H)-benzothiazolylidene)-1-propenyl] tetraiodide;

Benzothiazolium 2,2'-[1,3-propanediylbis[(dimethyliminio)-3,1-propanediyl-1(4H)-pyridinyl-4-ylidenemethylidyne]]bis[3-methyl] tetraiodide;

Benzoxazolium 2,2'-[1,3-propanediylbis[(dimethyliminio)-2,1-ethanediyl-1(4H)-quinolinyl-4-ylidene-1-propen-1-yl-3-ylidene]]bis[3-methyl] tetraiodide;

Quinolinium 1,1'-[1,3-propanediylbis[(dimethyliminio)-3,1-propanediyl]]bis[4-[3-(3-methyl-2(3H)-benzoxazolylidene)-1-propenyl] tetraiodide;

Phenanthridinium 5,5'-[1,2-ethanediylbis[(dimethyliminio)-3,1-propanediyl]]bis[3,8-diamino-6-phenyl] tetraiodide;

Dimethylenebis[2-({4-[(4-dimethylaminophenyl)(cyclohexa-2,5-dienylidene}-4-dimethylammonium)methylene]phenyl}ethylamino)-ethyl]dimethylammonium; and Tetramethylenebis[2-({4-[(4-dimethylaminophenyl)(cyclohexa-2,5-dienylidene}-4-dimethylammonium)methylene]phenyl}ethylamino)-ethyl]dimethylammonium.

The concentration of the at least one polycationic direct dyes of formula (I) may range from 0.001% to 5%, such as from 0.05% to 2% by weight relative to the total weight of the dye composition.

The compositions may, for example, comprise at least one cosmetic adjuvant, which may be chosen from monoalcohols such as alkanols, polyols, anionic, cationic, nonionic, amphoteric and zwitterionic surfactants, mineral thickeners, organic thickeners, and anionic, cationic, nonionic, and amphoteric associative polymers.

The organic thickeners may be chosen at least one of:
(i) associative thickeners;
(ii) crosslinked acrylic acid homopolymers;
(iii) crosslinked copolymers of (meth)acrylic acid and of $(C_1-C_6)$alkyl acrylate;
(iv) nonionic homopolymers and copolymers comprising at least one of ethylenically unsaturated ester monomers and ethylenically unsaturated amide monomers;
(v) ammonium acrylate homopolymers and copolymers of ammonium acrylate and of acrylamide;
(vi) polysaccharides; and
(vii) $C_{12}-C_{30}$ fatty alcohols.

As used herein, the expression "associative thickener" means an amphiphilic thickener comprising both hydrophilic units and hydrophobic units, for example, comprising at least one $C_8-C_{30}$ fatty chain and at least one hydrophilic unit.

Associative thickeners disclosed herein that may be used are associative polymers chosen from:
(i) nonionic amphiphilic polymers comprising at least one fatty chain and at least one hydrophilic unit;
(ii) anionic amphiphilic polymers comprising at least one hydrophilic unit and at least one fatty-chain unit;
(iii) cationic amphiphilic polymers comprising at least one hydrophilic unit and at least one fatty-chain unit; and
(iv) amphoteric amphiphilic polymers comprising at least one hydrophilic unit and at least one fatty-chain unit;
wherein the fatty chain unit contains from 10 to 30 carbon atoms.

The nonionic amphiphilic polymers comprising at least one fatty chain and at least one hydrophilic unit may be chosen from one or more of:
(1) celluloses modified with groups comprising at least one fatty chain; examples that may be mentioned include:
hydroxyethylcelluloses modified with at least one group comprising at least one fatty chain, for example, the at least one group may be chosen from alkyl, arylalkyl, and alkylaryl groups, and in which the alkyl groups may be $C_8-C_{22}$, such as the product NATROSOL® Plus Grade 330 CS, comprising $C_{16}$ alkyls, sold by the company Aqualon, or the product BERMOCOLL® EHM 100 sold by the company Berol Nobel, cellulloses modified with at least one polyalkylene glycol alkylphenyl ether group, such as the product AMER-CELL® Polymer HM-1500, comprising polyethylene glycol (15) nonylphenyl ether, sold by the company Amerchol.

(2) hydroxypropyl guars modified with at least one group comprising at least one fatty chain, such as the product ESAFLOR® HM 22, comprising $C_{22}$ alkyl chains, sold by the company Lamberti, and the products MIRA-CARE® XC95-3, comprising $C_{14}$ alkyl chains, and RE205-1, comprising $C_{20}$ alkyl chains, sold by the company Rhodia Chimie.

(3) polyether urethanes comprising at least one fatty chain, such as $C_{10}$–$C_{30}$ alkyl and alkenyl groups, for instance the products DAPRAL® T 210 and DAPRAL® T 212 sold by the company Akzo and the products ACULYN® 44 and ACULYN® 46 sold by the company Rohm & Haas.

(4) copolymers of vinylpyrrolidone and of hydrophobic fatty-chain monomers; examples that may be mentioned include:

the products ANTARON® V216 and GANEX® V216, comprising vinylpyrrolidone/hexadecene copolymers, sold by the company I.S.P.;

the products ANTARON® V220 and GANEX® V220, comprising vinylpyrrolidone/eicosene copolymers, sold by the company I.S.P.;

(5) copolymers of $C_1$–$C_6$ alkyl acrylates and methacrylates and of amphiphilic monomers comprising at least one fatty chain, such as, for example, the oxyethylenated methyl methacrylate/stearyl acrylate copolymer sold by the company Goldschmidt under the name ANTIL® 208; and (6) copolymers of hydrophilic acrylates and methacrylates and of hydrophobic monomers comprising at least one fatty chain, such as, for example, the polyethylene glycol methacrylate/lauryl methacrylate copolymer.

Among the anionic amphiphilic polymers disclosed herein comprising at least one hydrophilic unit and at least one fatty-chain unit, mention may be made of those comprising at least one fatty-chain allyl ether unit and at least one hydrophilic unit comprising an ethylenic unsaturated anionic monomer, such as those comprising at least one of vinylcarboxylic acid, acrylic acid, and methacrylic acid, , wherein the fatty-chain allyl ether unit corresponds to the monomer of formula (V) below:

$$CH_2=C(R5)CH_2OB_qR \qquad (V)$$

in which R5 is chosen from hydrogen atoms and methyl groups;

B denotes an ethyleneoxy radical;

q is chosen from integers ranging from 0 to 100; and R denotes a hydrocarbon-based radical chosen from alkyl, arylalkyl, aryl, alkylaryl, and cycloalkyl radicals, containing from 10 to 30 carbon atoms, such as 10 to 24 carbon atoms and further such as 12 to 18 carbon atoms.

A unit of formula (V) that may be used according to certain embodiments is a unit in which R5 denotes H, q is equal to 10, and R denotes a stearyl, i.e., $C_{18}$, radical.

Anionic amphiphilic polymers of this type are described and prepared, for example, according to an emulsion polymerization process in European Patent No. EP-0 216 479 B2.

Among these anionic amphiphilic polymers that may be used according to one embodiment are polymers formed from 20% to 60% by weight of acrylic acid and/or of methacrylic acid, from 5% to 60% by weight of lower alkyl (meth)acrylates, from 2% to 50% by weight of the at least one fatty-chain allyl ether of formula (V), and from 0% to 1% by weight of a crosslinking agent which comprise one or more well-known copolymerizable unsaturated polyethylenic monomers, for instance diallyl phthalate, allyl (meth) acrylate, divinylbenzene, (poly)ethylene glycol dimethacrylate, and methylenebisacrylamide.

Among the latter polymers, those that may be used include crosslinked terpolymers of methacrylic acid, of ethyl acrylate and of polyethylene glycol (10 EO) stearyl ether (Steareth-10), such as those sold by the company Ciba under the names SALCARE® SC 80 and SALCARE® SC 90, which are aqueous 30% emulsions of a crosslinked terpolymer of 40% methacrylic acid, of 50% ethyl acrylate, and of 10% steareth-10 allyl ether.

The anionic amphiphilic polymers can also be chosen from those comprising at least one unsaturated olefinic carboxylic acid hydrophilic unit, and at least one hydrophobic unit of the type such as a ($C_{10}$–$C_{30}$) alkyl ester of an unsaturated carboxylic acid, which, according to one embodiment, may be chosen from those in which the unsaturated olefinic carboxylic acid hydrophilic unit corresponds to the monomer of formula (VI) below:

in which

R6 is chosen from hydrogen atoms, methyl groups, and ethyl groups, such as acrylic acid, methacrylic acid, and ethacrylic acid units, and in which the hydrophobic unit of the type such as a ($C_{10}$–$C_{30}$) alkyl ester of an unsaturated carboxylic acid corresponds to the monomer of formula (VII) below:

$$H_2C=CR6\text{-}CO\text{—}OR7 \qquad (VII)$$

in which formula R6 is chosen from hydrogen atoms, methyl groups, and ethyl groups, such as acrylate, methacrylate, and ethacrylate units, and such as hydrogen atoms, i.e., acrylate units, and methyl groups, i.e., methacrylate units; and R7 is a $C_{10}$–$C_{30}$, such as $C_{12}$–$C_{22}$, alkyl radical.

($C_{10}$–$C_{30}$)Alkyl esters of unsaturated carboxylic acids disclosed herein comprise, for example, at least one of lauryl acrylate, stearyl acrylate, decyl acrylate, isodecyl acrylate, dodecyl acrylate, and the corresponding methacrylates, lauryl methacrylate, stearyl methacrylate, decyl methacrylate, isodecyl methacrylate, and dodecyl methacrylate.

Anionic amphiphilic polymers of this type are disclosed and prepared, for example, according to U.S. Pat. Nos. 3,915,921 and 4,509,949.

The anionic amphiphilic polymers that may be used in the composition disclosed herein may for example comprise polymers formed from a mixture of monomers. The anionic amphiphilic polymers may comprise at least one of the following monomers:

(i) acrylic acid, an ester of formula (VIII) below:

$$H_2C=CR8\text{-}CO\text{—}OR9 \qquad (VIII)$$

in which R8 is chosen from hydrogen atoms and methyl groups, R9 is an alkyl radical containing from 12 to 22 carbon atoms, and a crosslinking agent, such as, for example, those comprising from 95% to 60% by weight of acrylic acid, i.e., a hydrophilic unit, 4% to 40% by weight of $C_{10}$–$C_{30}$ alkyl acrylate, i.e., a hydrophobic unit, and 0% to 6% by weight of crosslinking polymerizable monomer, or 98% to 96% by weight of acrylic acid, i.e., a hydrophilic unit, 1% to 4% by weight of $C_{10}$–$C_{30}$ alkyl acrylate, i.e., a hydrophobic unit, and 0.1% to 0.6% by weight of crosslinking polymerizable monomer; and (ii) acrylic acid and lauryl methacrylate, such as the product formed from 66% by weight of acrylic acid and 34% by weight of lauryl methacrylate.

The said crosslinking agent is a monomer containing a group

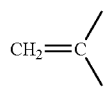

with at least one other polymerizable group whose unsaturated bonds are not conjugated. Mention may be made for example of polyallyl ethers such as polyallylsucrose and polyallylpentaerythritol.

Among the said polymers above, ones that may be used according to one embodiment are the products sold by the company Goodrich under the trade names PEMULEN® TR1, PEMULEN® TR2, CARBOPOL® 1382, such as, for example, PEMULEN® TR1, and the product sold by the company S.E.P.C. under the name COATEX® SX.

As anionic amphiphilic fatty-chain polymers, mention may also be made of the ethoxylated copolymer of methacrylic acid/methyl acrylate/alkyl dimethyl-meta-isopropenylbenzylisocyanate sold under the name VISCOPHOBE® DB 1000 by the company Amerchol.

The cationic amphiphilic polymers disclosed herein may be chosen from at least one of quaternized cellulose derivatives and polyacrylates containing amino side groups.

The quaternized cellulose derivatives comprise, for example, quaternized celluloses modified with at least one group comprising at least one fatty chain, such as alkyl, arylalkyl, and alkylaryl groups containing at least 8 carbon atoms, and quaternized hydroxyethylcelluloses modified with at least one group comprising at least one fatty chain, such as alkyl, arylalkyl, and alkylaryl groups containing at least 8 carbon atoms.

Quaternized or non-quaternized polyacrylates containing amino side groups, have, for example, hydrophobic groups, such as STEARETH® 20, comprising polyoxyethylenated (20) stearyl alcohol, and ($C_{10}$–$C_{30}$)alkyl PEG-20 itaconate.

The alkyl radicals borne by the above quaternized celluloses or hydroxyethylcelluloses may contain from 8 to 30 carbon atoms.

The aryl radicals may be chosen from phenyl, benzyl, naphthyl, and anthryl groups.

Quaternized alkylhydroxyethylcelluloses containing $C_8$–$C_{30}$ fatty chains may be chosen from one or more of the products QUATRISOFT® LM 200, QUATRISOFT® LM-X 529-18-A, QUATRISOFT® LM-X 529-18B, comprising C12 alkyls, and QUATRISOFT® LM-X 529-8, comprising $C_{18}$ alkyls, sold by the company Amerchol, and the products CRODACEL® QM, CRODACEL® QL, comprising $C_{12}$ alkyls, and CRODACEL® QS, comprising $C_{18}$ alkyls, sold by the company Croda.

Polyacrylates comprising amino side chains may be chosen from at least one of the polymers 8781-124B, 9492-103, and Structure Plus from the company National Starch.

Amphoteric amphiphilic polymers comprising at least one fatty chain, may be chosen from one or more of copolymers of methacrylamidopropyltrimethylammonium chloride/acrylic acid/C10–C30 alkyl methacrylate, the alkyl radical for example being a stearyl radical.

In certain embodiments, the associative thickeners in the cosmetic compositions disclosed herein have, in solution or in dispersion at a concentration of 1% active material in water, a viscosity, measured using a Rheomat RM 180 rheometer at 25° C., of greater than 0.1 ps, or for example of greater than 0.2 cp, at a shear rate of 200 $s^{-1}$.

(i) Among the crosslinked acrylic acid homopolymers that may be mentioned are those crosslinked with an allylic alcohol ether of the sugar series, such as, for example, the products sold under the names CARBOPOL® 980, 981, 954, 2984, and 5984 by the company Goodrich or the products sold under the names SYNTHALEN® M and SYNTHALEN® K by the company 3 VSA.

(ii) Among the crosslinked copolymers of (meth)acrylic acid and of $C_1$–$C_6$ alkyl acrylate that may be mentioned is the product sold under the name VISCOATEX® 538C by the company Coatex, which is a crosslinked copolymer of methacrylic acid and of ethyl acrylate as an aqueous dispersion containing 38% active material, and the product sold under the name ACULYN® 33 by the company Rohm & Haas, which is a crosslinked copolymer of acrylic acid and of ethyl acrylate as an aqueous dispersion containing 28% active material.

(iii) Among the nonionic homopolymers or copolymers comprising at least one of ethylenically unsaturated ester monomers and ethylenically unsaturated amide monomers, mention may be made of the products sold under the names: CYANAMER® P250 by the company Cytec, comprising polyacrylamide; PMMA MBX-8C by the company U.S. Cosmetics, comprising methyl methacrylate/ethylene glycol dimethacrylate copolymers; ACRYLOID® B66 by the company Rohm & Haas, comprising butyl methacrylate/methyl methacrylate copolymers; and BPA 500 by the company Kobo, comprising polymethyl methacrylate.

(iv) Among the ammonium acrylate homopolymers that may be mentioned is the product sold under the name MICROSAP® PAS 5193 by the company Hoechst.

Copolymers of ammonium acrylate and of acrylamide may be, for example, chosen from one or more of the product sold under the name Bozepol C Nouveau or the product PAS 5193 sold by the company Hoechst, which are described and prepared for example in documents French Patent FR 2 416 723, and U.S. Pat. Nos. 2,798,053 and 2,923,692.

(v) The thickening polysaccharides may be chosen from at least one of glucans; modified or unmodified starches, such as those derived, for example, from cereals, for instance wheat, corn, and rice, from vegetables, for instance yellow pea, and tubers, for instance potato and cassava; amylose; amylopectin; glycogen; dextrans; celluloses and derivatives thereof, such as methylcelluloses, hydroxyalkylcelluloses, ethylhydroxyethylcelluloses, and carboxymethylcelluloses; mannans; xylans; lignins; arabans; galactans; galacturonans; chitin; chitosans; glucuronoxylans; arabinoxylans; xyloglucans; glucomannans; pectic acids, pectins; alginic acid; alginates; arabinogalactans; carrageenans; agars; glycosaminoglucans; gum arabics; gum tragacanths; ghatti gums; karaya gums; carob gums; and galactomannans, such as guar gums and nonionic derivatives thereof, for instant hydroxypropyl guar and xanthan gums.

In general, the compounds of this type that may be used according to certain embodiments disclosed herein are chosen from those described for example in "Encyclopedia of Chemical Technology", Kirk-Othmer, Third Edition, 1982, volume 3, pp. 896–900, and volume 15, pp. 439–458, in "Polymers in Nature" by E. A. MacGregor and C. T. Greenwood, published by John Wiley & Sons, Chapter 6, pp. 240–328, 1980, and in "Industrial Gums—Polysaccharides and their Derivatives", edited by Roy L. Whistler, Second Edition, published by Academic Press Inc. The content of these three publications is incorporated by reference herein.

Starches, guar gums, celluloses, and derivatives thereof may, for example, be used.

The guar gums may be modified or unmodified.

Unmodified guar gums may be, for example, chosen from at least one of the products sold under the name VIDOGUM® GH 175 by the company Unipectine and under the names MEYPRO®-GUAR 50 and JAGUAR® C by the company Meyhall.

The modified nonionic guar gums may be modified with $C_1$–$C_6$ hydroxyalkyl groups.

Hydroxyalkyl groups may be, for example, chosen from one or more of hydroxymethyl, hydroxyethyl, hydroxypropyl, and hydroxybutyl groups. These guar gums are known in the prior art and can be prepared, for example, by reacting the corresponding alkene oxides such as, for example, propylene oxides, with the guar gum so as to obtain a guar gum modified with hydroxypropyl groups.

The degree of hydroxyalkylation, which corresponds to the number of alkylene oxide molecules consumed by the number of free hydroxyl functions present on the guar gum, may range from 0.4 to 1.2.

Such nonionic guar gums optionally modified with hydroxyalkyl groups are sold, for example, under the trade names JAGUAR® HP8, JAGUAR® HP60, JAGUAR® HP120, JAGUAR® DC 293, and JAGUAR HP 105 by the company RhodiaCelluloses may be, for example, chosen from at least one of hydroxyethylcelluloses and hydroxypropylcelluloses. Mention may be made of the products sold under the names KLUCEL® EF, KLUCEL® H, KLUCEL® LHF, KLUCEL® MF, and KLUCEL® G by the company Aqualon.

The fatty alcohols may be chosen from one or more of myristyl alcohol, cetyl alcohol, stearyl alcohol, and behenyl alcohol.

Mineral thickeners may be chosen from one or more clays.

As disclosed herein, the thickeners may range from 0.001% to 20% by weight, such as from 0.01% to 10% by weight or from 0.1% to 3% by weight, relative to the total weight of the final composition.

The compositions of the invention may also comprise at least one surfactant, which is generally present in an amount ranging from 0.1% to 60% by weight, such as from 3% to 40% or from 5% to 30%, relative to the total weight of the composition.

Surfactants may be chosen from one or more of anionic, amphoteric, nonionic, and cationic surfactants.

Surfactants suitable for carrying out the present invention may, for example, be chosen from one or more of the following:

(i) Anionic Surfactants:

According to certain embodiments disclosed herein, the nature of the anionic surfactants may not be a critical factor. Thus, examples of anionic surfactants may be chosen from at least one of the following non-limiting list, of salts, such as alkaline salts, including sodium salts, ammonium salts, amine salts, amino alcohol salts, and magnesium salts, of the following compounds: alkyl sulphates, alkyl ether sulphates, alkylamido ether sulphates, alkylarylpolyether sulphates, monoglyceride sulphates, alkyl sulphonates, alkyl phosphates, alkylamide sulphonates, alkylaryl sulphonates, α-olefin sulphonates, paraffin sulphonates, alkyl sulphosuccinates, alkyl ether sulphosuccinates, alkylamide sulphosuccinates, alkyl sulphosuccinamates, alkyl sulphoacetates, alkyl ether phosphates, acyl sarcosinates, acyl isethionates, and N-acyltaurates, wherein at least one of the alkyl and acyl radicals of all of these various compounds may for example comprise from 8 to 24 carbon atoms, and the aryl radical may be chosen from phenyl and benzyl groups. Among the anionic surfactants which can also be used, mention may also be made of fatty acid salts such as the salts of oleic acid, ricinoleic acid, palmitic acid, stearic acids, coconut oil acid, hydrogenated coconut oil acid; and acyl lactylates in which the acyl radical contains 8 to 20 carbon atoms. Weakly anionic surfactants can also be used, such as at least one of alkyl-D-galactosiduronic acids and their salts, polyoxyalkylenated ($C_6$–$C_{24}$) alkyl ether carboxylic acids, polyoxyalkylenated ($C_6$–$C_{24}$) alkylaryl ether carboxylic acids, and polyoxyalkylenated ($C_6$–$C_{24}$) alkylamido ether carboxylic acids and their salts, such as those containing from 2 to 50 ethylene oxide groups.

The anionic surfactants, may, for example, be chosen from at least one of alkyl sulphate salts and alkyl ether sulphate salts (ii) Nonionic Surfactants:

The nonionic surfactants are compounds that may be known per se. See for example in this respect "Handbook of Surfactants" by M. R. Porter, published by Blackie & Son (Glasgow and London), 1991, pp. 116–178. As disclosed herein, their nature may not be a critical feature. Thus, they may be chosen for example from, as a non-limiting list: polyethoxylated fatty acids, polypropoxylated fatty acids, polyglycerolated fatty acids, alkylphenols, α-diols, and alcohols having a fatty chain containing, for example, 8 to 18 carbon atoms, it being possible for the number of ethylene oxide or propylene oxide groups to range from 2 to 50 and for the number of glycerol groups to range from 2 to 30. Mention may also be made of copolymers of ethylene oxide and of propylene oxide, condensates of ethylene oxide and of propylene oxide with fatty alcohols; polyethoxylated fatty amides having, for example, from 2 to 30 mol of ethylene oxide, polyglycerolated fatty amides containing on average 1 to 5, such as 1.5 to 4, glycerol groups; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$–$C_{14}$) alkylamine oxides, and N-acylaminopropylmorpholine oxides. It will be noted that the alkylpolyglycosides constitute nonionic surfactants may be used according to certain embodiments.

(iii) Amphoteric Surfactants:

The amphoteric surfactants, whose nature may not be a critical feature as disclosed herein, may be chosen from at least one of, for example as a non-limiting list: aliphatic secondary or tertiary amine derivatives in which the aliphatic radical is a linear or branched chain containing 8 to 22 carbon atoms and comprising at least one water-soluble anionic group, for example carboxylate, sulphonate, sulphate, phosphate, and phosphonate. Mention may also be made of ($C_8$–$C_{20}$)alkylbetaines, sulphobetaines, ($C_8$–$C_{20}$) alkylamido($C_1$–$C_6$)alkylbetaines, and ($C_8$–$C_{20}$)alkylamido ($C_1$–$C_6$)alkylsulphobetaines.

Among the amine derivatives, mention may be made of the products sold under the name MIRANOL®, as described in U.S. Pat. Nos. 2,528,378 and 2,781,354 and having the structures:

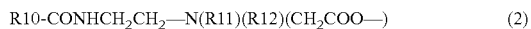

$$R10\text{-}CONHCH_2CH_2\text{—}N(R11)(R12)(CH_2COO\text{—}) \quad (2)$$

in which: R10 is chosen from linear or branched $C_5$–$C_{20}$ alkyl radical derived from an acid
R10-COOH present in hydrolyzed coconut oil, heptyl, nonyl, and undecyl radicals;
R11 denotes a β-hydroxyethyl group; and
R12 denotes a carboxymethyl group; and

$$R13\text{-}CONHCH_2CH_2\text{—}N(D)(E) \quad (3)$$

in which:
D represents —$CH_2CH_2OX'$;
E represents —$(CH_2)_z$—Y', wherein z is chosen from 1 and 2;
X' is chosen from —$CH_2CH_2$—COOH groups and hydrogen atoms;
Y' is chosen from —COOH and —$CH_2$—CHOH—$SO_3H$ radicals;
R13 is chosen from linear or branched, saturated or unsaturated $C_5$–$C_{20}$ alkyl radicals of an acid R13-COOH present in, for example, at least one of coconut oil and hydrolyzed linseed oil, alkyl radicals, such as $C_7$, $C_9$, $C_{11}$, and $C_{13}$ alkyl radicals, $C_{17}$ alkyl radicals and its iso form, and unsaturated $C_{17}$ radicals.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium caprylamphodipropionate, lauroamphodipropionic acid, and cocoamphodipropionic acid.

By way of example, mention may be made of the cocoamphodiacetate sold under the trade name MIRANOL® C2M Concentrate by the company Rhodia Chimie.

(iv) Cationic Surfactants:

The cationic surfactants may be chosen from:
A) the quaternary ammonium salts of general formula (XII) below:

in which X⁻ is an anion chosen from halides such as chloride, bromide, and iodide, ($C_2$–$C_6$)alkyl sulphates, such as methyl sulphate, phosphates, alkyl sulphonates, alkylaryl sulphonates, and anions derived from organic acid, such as acetate and lactate; and
  i) the radicals R14 to R16, which may be identical or different, are chosen from linear or branched aliphatic radicals containing from 1 to 4 carbon atoms, and aromatic radicals such as aryl and alkylaryl. The aliphatic radicals can comprise hetero atoms such as oxygen, nitrogen, sulphur, and halogens. The aliphatic radicals may be chosen, for example, from alkyl, alkoxy, and alkylamide radicals;
R17 is chosen from linear or branched alkyl radicals containing from 16 to 30 carbon atoms.

The cationic surfactant may be a behenyltrimethylammonium salt, for example chloride.
  ii) the radicals R14 and R15, which may be identical or different, are chosen from linear or branched aliphatic radicals containing from 1 to 4 carbon atoms, and aromatic radicals such as aryls and alkylaryls. The aliphatic radicals may comprise hetero atoms such as oxygen, nitrogen, sulphur, and halogens. The aliphatic radicals may be chosen, for example, from alkyl, alkoxy, alkylamide, and hydroxyalkyl radicals containing from 1 to 4 carbon atoms;
R16 and R17, which may be identical or different, are chosen from linear or branched alkyl radicals containing from 12 to 30 carbon atoms, the said radicals comprising at least one of ester and amide functional groups.

R16 and R17 may be chosen from ($C_{12}$–$C_{22}$)alkylamido ($C_2$–$C_6$)alkyl and ($C_{12}$–$C_{22}$)alkylacetate radicals.

The cationic surfactant may be a stearamidopropyldimethyl(myristyl acetate)ammonium salt, for example chloride;

B)—the quaternary ammonium salts of imidazolinium, such as, for example, that of formula (XIII) below:

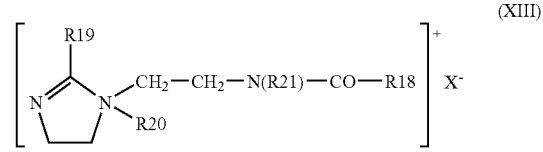

in which R18 is chosen from alkenyl and alkyl radicals containing from 8 to 30 carbon atoms, for example fatty acid derivatives of tallow; R19 is chosen from hydrogen atoms, $C_1$–$C_4$ alkyl radicals, and alkenyl and alkyl radicals containing from 8 to 30 carbon atoms; R20 represents a $C_1$–$C_4$ alkyl radical; R21 is chosen from hydrogen atoms and $C_1$–$C_4$ alkyl radicals; and X is an anion chosen from halides, phosphates, acetates, lactates, alkyl sulphates, alkyl sulphonates, and alkylaryl sulphonates. R18 and R19 may, for example, be chosen from a mixture of alkenyl and alkyl radicals containing from 12 to 21 carbon atoms, such as, for example, fatty acid derivatives of tallow; R20 may denote methyl; and R21 may denote hydrogen. Such a product is, for example, Quaternium-27. (CTFA 1997) or Quaternium-83 (CTFA 1997), which are sold under the names REWO-QUAT W75, W90, W75PG, and W75HPG by the company Witco;

C)—the diquaternary ammonium salts of formula (XIV):

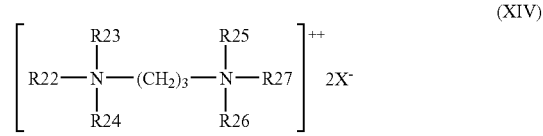

in which R22 is chosen from aliphatic radicals containing from 16 to 30 carbon atoms; R23, R24, R25, R26, and R28, which may be identical or different, are chosen from hydrogen atoms and alkyl radicals containing from 1 to 4 carbon atoms; and X is an anion chosen from halides, acetates, phosphates, nitrates, and methyl sulphates. Such diquaternary ammonium salts may, for example, comprise propanetallowdiammonium dichloride;

D)—the quaternary ammonium salts comprising at least one ester function, of formula (XV) below:

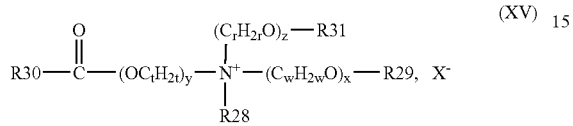

in which:

R28 is chosen from $C_1$–$C_6$ alkyl radicals, $C_1$–$C_6$ hydroxyalkyl radicals, and dihydroxyalkyl radicals;

R29 is chosen from:

radicals

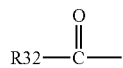

linear or branched, saturated or unsaturated $C_1$–$C_{22}$ hydrocarbon-based radicals R33, and hydrogen atoms, R31 is chosen from:

a radical

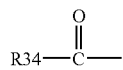

linear or branched, saturated or unsaturated $C_1$–$C_6$ hydrocarbon-based radicals R35, hydrogen atoms, R30, R32, and R34, which may be identical or different, are chosen from linear or branched, saturated or unsaturated $C_7$–$C_{21}$ hydrocarbon-based radicals;

t, w, and r, which may be identical or different, are chosen from integers ranging from 2 to 6;

y is an integer ranging from 1 to 10;

x and z, which may be identical or different, are chosen from integers ranging from 0 to 10; and $X^-$ is chosen from simple or complex, organic or inorganic anions; with the proviso that the sum x+y+z ranges from 1 to 15, that when x is 0, then R29 denotes R33, and that when z is 0, then R31 denotes R35.

Use may be made, for example, of the ammonium salts of formula (XV) in which:

R28 is chosen from methyl and ethyl radicals;

x and y are equal to 1;

z is chosen from 0 and 1;

t, w, and r are equal to 2;

R29 is chosen from:
radicals

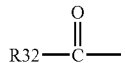

methyl, ethyl, and $C_{14}$–$C_{22}$ hydrocarbon-based radicals, hydrogen atoms;

R30, R32, and R34, which may be identical or different, are chosen from linear or branched, saturated or unsaturated $C_7$–$C_{21}$ hydrocarbon-based radicals; and R31 is chosen from:
radicals

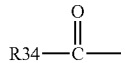

hydrogen atoms.

Such compounds are sold, for example, under the names DEHYQUART® by the company Cognis, STEPANQUAT® by the company Stepan, NOXAMIUM® by the company Ceca, and REWOQUAT® 18 by the company Rewo-Witco.

Among the quaternary ammonium salts that may be used are behenyltrimethylammonium chloride and stearamidopropyldimethyl(myristyl acetate)ammonium chloride, sold under the name CERAPHYL® 70 by the company Van Dyk, and Quaternium-27 or Quaternium-83 sold by the company Witco.

In certain embodiments, an anionic surfactant may be chosen from sodium, triethanolamine, and ammonium ($C_{12}$–$C_{14}$)alkyl sulphates; sodium, triethanolamine, and ammonium ($C_{12}$–$C_{14}$)alkyl ether sulphates oxyethylenated with 2.2 mol of ethylene oxide; sodium cocoyl isethionate and sodium α-($C_{14}$–$C_{16}$)olefin sulphonate, and mixtures thereof, with:

at least one of amphoteric surfactants such as the amine derivatives known as disodium cocoamphodipropionate or sodium cocoamphopropionate sold especially by the company Rhodia Chimie under the trade name MIRANOL® C2M CONC as an aqueous solution containing 38% active material, and under the name MIRANOL® C32;

and amphoteric surfactants such as alkylbetaines, for example, the cocobetaine sold under the name DEHYTON® AB 30 as an aqueous solution containing 32% AM by the company Cognis, and ($C_8$–$C_{20}$)alkylamido ($C_1$–$C_6$)alkylbetaines, such as TEGOBETAINE® F50 sold by the company Goldschmidt.

For the alkanols, compounds that may be mentioned are linear or branched C1–C4 alkanols such as ethanol and isopropanol.

The polyols may have a molecular mass of less than 1000. They may also be linear or branched and may contain from 2 to 10 hydroxyl functions. Among these polyols, mention may be made of propylene glycol, glycerol, hexylene glycol, neopentyl glycol, isoprene glycol, 1,4-butanediol, 2-methyl-1,3-propanediol, and polyethylene glycols.

The adjuvants described may generally be present in an amount for each one ranging from 0.01% to 20% by weight relative to the weight of the composition.

The dye composition disclosed herein may also comprise additional direct dyes other than those of formula (1), which may be chosen from neutral, acidic, and cationic nitrobenzene direct dyes; neutral, acidic, and cationic azo direct dyes; neutral, acidic, and cationic quinone, such as anthraquinone direct dyes, azine direct dyes, methine direct dyes, triarylmethane direct dyes, indoamine direct dyes, and natural direct dyes.

The benzenic direct dyes, may, for example, be chosen from one or more of the following compounds:
1,4-diamino-2-nitrobenzene;
1-amino-2-nitro-4-(β-hydroxyethylamino)benzene;
1-amino-2-nitro-4-bis(β-hydroxyethyl)aminobenzene;
1,4-bis(β-hydroxyethylamino)-2-nitrobenzene;
1-β-hydroxyethylamino-2-nitro-4-bis(β-hydroxyethylamino)benzene;
1-β-hydroxyethylamino-2-nitro-4-aminobenzene;
1-β-hydroxyethylamino-2-nitro-4-(ethyl)(β-hydroxyethyl)aminobenzene;
1-amino-3-methyl-4-β-hydroxyethylamino-6-nitrobenzene;
1-amino-2-nitro-4-β-hydroxyethylamino-5-chlorobenzene;
1,2-diamino-4-nitrobenzene;
1-amino-2-β-hydroxyethylamino-5-nitrobenzene;
1,2-bis(β-hydroxyethylamino)-4-nitrobenzene;
1-amino-2-[tris(hydroxymethyl)methylamino]-5-nitrobenzene;
1-hydroxy-2-amino-5-nitrobenzene;
1-hydroxy-2-amino-4-nitrobenzene;
1-hydroxy-3-nitro-4-aminobenzene;
1-hydroxy-2-amino-4,6-dinitrobenzene;
1-β-hydroxyethyloxy-2-β-hydroxyethylamino-5-nitrobenzene;
1-methoxy-2-β-hydroxyethylamino-5-nitrobenzene;
1-β-hydroxyethyloxy-3-methylamino-4-nitrobenzene;
1-β,γ-dihydroxypropyloxy-3-methylamino-4-nitrobenzene;
1-β-hydroxyethylamino-4-β,γ-dihydroxypropyloxy-2-nitrobenzene;
1-β,γ-dihydroxypropylamino-4-trifluoromethyl-2-nitrobenzene;
1-β-hydroxyethylamino-4-trifluoromethyl-2-nitrobenzene;
1-β-hydroxyethylamino-3-methyl-2-nitrobenzene;
1-β-aminoethylamino-5-methoxy-2-nitrobenzene;
1-hydroxy-2-chloro-6-ethylamino-4-nitrobenzene;
1-hydroxy-2-chloro-6-amino-4-nitrobenzene;
1-hydroxy-6-[bis(β-hydroxyethyl)amino]-3-nitrobenzene;
1-β-hydroxyethylamino-2-nitrobenzene; and
1-hydroxy-4-β-hydroxyethylamino-3-nitrobenzene.

The azo direct dyes may, for example, be chosen from one or more of the cationic azo dyes described, for example, in Patent Applications WO 95/15144, WO 95/01772, EP 714 954, and WO 01/66646. The passages in these applications which relate to azo direct dyes are incorporated herein by reference.

Theazo direct dyes may, for example, be chosen from one or more of the following dyes:
1,3-dimethyl-2-[[4-(dimethylamino)phenyl]azo]-1H-imidazolium chloride;
1,3-dimethyl-2-[(4-aminophenyl)azo]-1H-imidazolium chloride; and
1-methyl-4-[(methylphenylhydrazono)methyl]pyridinium methyl sulphate.

The azo direct dyes may, for example, also be chosen from at least one of the following dyes described, for example, in the Colour Index International 3rd edition:
Disperse Red 17;
Acid Yellow 9;
Acid Black 1;
Basic Red 22;
Basic Red 76;
Basic Yellow 57;
Basic Brown 16;
Acid Yellow 36;
Acid Orange 7;
Acid Red 33;
Acid Red 35;
Basic Brown 17;
Acid Yellow 23;
Acid Orange 24; and
Disperse Black 9.

Azo dyes may additionally be chosen from at least one of 1-(4'-aminodiphenylazo)-2-methyl-4-[bis(β-hydroxyethyl)amino]benzene and 4-hydroxy-3-(2-methoxyphenylazo)-1-naphthalenesulphonic acid.

The quinone direct dyes may, for example, be chosen from one or more of the following dyes:
Disperse Red 15;
Solvent Violet 13;
Acid Violet 43;
Disperse Violet 1;
Disperse Violet 4;
Disperse Blue 1;
Disperse Violet 8;
Disperse Blue 3;
Disperse Red 11;
Acid Blue 62;
Disperse Blue 7;
Basic Blue 22;
Disperse Violet 15;
Basic Blue 99;
and also the following compounds:
    1-N-methylmorpholiniumpropylamino-4-hydroxyanthraquinone;
    1-aminopropylamino-4-methylaminoanthraquinone;
    1-aminopropylaminoanthraquinone;
    5-β-hydroxyethyl-1,4-diaminoanthraquinone;
    2-aminoethylaminoanthraquinone; and
    1,4-bis(β,γ-dihydroxypropylamino)anthraquinone.

The azine dyes may be, for example, chosen from one or more of the following compounds:
Basic Blue 17; and
Basic Red 2.

The triarylmethane dyes may be, for example, chosen from one or more of the following compounds:
Basic Green 1;
Acid Blue 9;
Basic Violet 3;
Basic Violet 14;
Basic Blue 7;
Acid Violet 49;
Basic Blue 26; and
Acid Blue 7.

The indoamine dyes may be, for example, chosen from one or more of the following compounds:
2-β-hydroxyethylamino-5-[bis(β-4'-hydroxyethyl)amino]anilino-1,4-benzoquinone;
2-β-hydroxyethylamino-5-(2'-methoxy-4'-amino)anilino-1,4-benzoquinone;
3-N(2'-chloro-4'-hydroxy)phenylacetylamino-6-methoxy-1,4-benzoquinoneimine;
3-N(3'-chloro-4'-methylamino)phenylureido-6-methyl-1,4-benzoquinoneimine; and
3-[4'-N-(ethylcarbamylmethyl)amino]phenylureido-6-methyl-1,4-benzoquinoneimine.

The natural direct dyes may be, for example chosen from at least one of lawsone, juglone, alizarin, purpurin, carminic acid, kermesic acid, purpurogallin, protocatechaldehyde, indigo, isatin, curcumin, spinulosin, and apigenidin. Extracts and decoctions comprising these natural dyes may also be used, such as henna-based poultices and extracts.

The total proportion of additional direct dyes may range from 0.001% to 20% by weight approximately, such as from 0.005% to 10% by weight approximately, relative to the total weight of the ready-to-use composition.

The composition of the invention may also comprise an oxidizing agent. This oxidizing agent may be any oxidizing agent conventionally used for bleaching human keratin fibers. The oxidizing agent may be chosen from at least one of hydrogen peroxide, urea peroxide, alkali metal bromates, persalts such as perborates and persulphates, peracids and enzymes, for example, peroxidases, 2-electron oxidoreductases such as uricases, and 4-electron oxygenases such as laccases. Mention may be made, for example, of the use of hydrogen peroxide.

When the composition disclosed herein is intended for standard oxidation dyeing, it may also comprise at least one oxidation base. This oxidation base may be chosen from the oxidation bases conventionally used in oxidation dyeing, for example one or more of para-phenylenediamines, bis(phenyl)alkylenediamines, para-aminophenols, ortho-aminophenols, and heterocyclic bases.

The para-phenylenediamines may be, for example, be chosen from at least one of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis($\beta$-hydroxyethyl)-para-phenylenediamine, 4-N,N-bis($\beta$-hydroxyethyl)amino-2-methylaniline, 4-N,N-bis($\beta$-hydroxyethyl)amino-2-chloroaniline, 2-$\beta$-hydroxyethyl-para-phenylenediamine, 2-fluoro-para-phenylenediamine, 2-isopropyl-para-phenylenediamine, N-($\beta$-hydroxypropyl)-para-phenylenediamine, 2-hydroxymethyl-para-phenylenediamine, N,N-dimethyl-3-methyl-para-phenylenediamine, N-ethyl-N-($\beta$-hydroxyethyl)-para-phenylenediamine, N-($\beta$,$\gamma$-dihydroxypropyl)-para-phenylenediamine, N-(4'-aminophenyl)-para-phenylenediamine, N-phenyl-para-phenylenediamine, 2-$\beta$-hydroxyethyloxy-para-phenylenediamine, 2-$\beta$-acetylaminoethyloxy-para-phenylenediamine, N-($\beta$-methoxyethyl)-para-phenylenediamine, 4-aminophenylpyrrolidine, 2-thienyl-para-phenylenediamine, 2-$\beta$-hydroxyethylamino-5-aminotoluene, and the acid addition salts thereof.

Of the para-phenylenediamines mentioned above, para-phenylenediamine, para-tolylenediamine, 2-isopropyl-para-phenylenediamine, 2-$\beta$-hydroxyethyl-para-phenylenediamine, 2-$\beta$-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis($\beta$-hydroxyethyl)-para-phenylenediamine, 2-chloro-para-phenylenediamine and 2-$\beta$-acetylaminoethyloxy-para-phenylenediamine, and the acid addition salts thereof may, for example, be further mentioned.

The bis(phenyl)alkylenediamines may, for example, be chosen from one or more of N,N'-bis($\beta$-hydroxyethyl)-N,N'-bis(4'-aminophenyl)-1,3-diaminopropanol, N,N'-bis($\beta$-hydroxyethyl)-N,N'-bis(4'-aminophenyl)ethylenediamine, N,N'-bis(4-aminophenyl)-tetramethylenediamine, N,N'-bis($\beta$-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine, 1,8-bis(2,5-diaminophenoxy)-3,6-dioxaoctane, and the acid addition salts thereof.

The para-aminophenols may, for example, be chosen from one or more of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-($\beta$-hydroxyethylaminomethyl)phenol, 4-amino-2-fluorophenol, and the acid addition salts thereof.

The ortho-aminophenols may, for example, be chosen from one or more of 2-aminophenol, 2-amino-5-methylphenol, 2-amino-6-methylphenol, 5-acetamido-2-aminophenol, and the acid addition salts thereof.

The heterocyclic bases may, for example, be chosen from one or more of pyridine derivatives, pyrimidine derivatives, and pyrazole derivatives.

The pyridine derivatives may, for example, be chosen from one or more of the compounds described, for example, in British Patent Nos. GB 1 026 978 and GB 1 153 196, as well as 2,5-diaminopyridine, 2-(4-methoxyphenyl)amino-3-aminopyridine, 2,3-diamino-6-methoxypyridine, 2-($\beta$-methoxyethyl)amino-3-amino-6-methoxypyridine, and 3,4-diaminopyridine, and the acid addition salts thereof.

The pyrimidine derivatives may, for example, be chosen from one or more of the compounds described, for example, in German Patent DE 2 359 399; Japanese Patents JP 88-169 571 and JP 05-163 124, European Patent EP 0 770 375, and Patent Application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in French Patent Application FR A 2 750 048 and, for example, pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl) amino]ethanol, 5,6-dimethyl-pyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylaminopyrazolo[1,5-a]pyrimidine, and the acid addition salts thereof and the tautomeric forms thereof, when a tautomeric equilibrium exists.

The pyrazole derivatives may, for example, be chosen from one or more of the compounds described in German Patents DE 3 843 892 and DE 4 133 957, and Patent Applications WO 94/08969, WO 94/08970, French Patent FR-A-2 733 749, and German Patent DE 195 43 988, such as 4,5-diamino-1-methylpyrazole, 4,5-diamino-1-($\beta$-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-($\beta$-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3- hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl) amino-1-methylpyrazole, and the acid addition salts thereof.

The composition disclosed herein may also comprise at least one coupler conventionally used for standard oxidation dyeing of human keratin fibers. These couplers, may, for example, be chosen from one or more of meta-phenylenediamines, meta-aminophenols, meta-diphenols, naphthalene-based couplers, and heterocyclic couplers.

Examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, and the acid addition salts thereof.

In the composition disclosed herein, the at least one coupler may generally be present in an amount ranging from 0.001% to 1.0% by weight, such as from 0.005% to 6% by weight, relative to the total weight of the dye composition. The at least one oxidation base may be present in an amount ranging from 0.001% to 10% by weight, such as from 0.005% to 6% by weight, relative to the total weight of the dye composition.

In general, the acid addition salts that may be used in the context of the dye compositions disclosed herein for the oxidation bases and couplers may be chosen from one or more of hydrochlorides, hydrobromides, sulphates, citrates, succinates, tartrates, lactates, tosylates, benzenesulphonates, phosphates, and acetates.

The medium that is cosmetically suitable for dyeing, also known as the dye support, may generally comprise water or a mixture of water and at least one organic solvent to dissolve the compounds that would not be sufficiently soluble in water. Organic solvents, may, for example, be chosen from one or more of $C_1$–$C_4$ lower alkanols, such as ethanol and isopropanol, as well as aromatic alcohols such as benzyl alcohol, phenoxyethanol, and mixtures thereof.

The solvents may be present in proportions ranging from 1% to 40% by weight relative to the total weight of the dye composition, such as from 5% to 30% by weight.

The dye composition disclosed herein may also comprise at least one adjuvants conventionally used in compositions for dyeing the hair, such as antioxidants, penetration agents, sequestering agents, fragrances, buffers, dispersing agents, anionic, cationic, nonionic, amphoteric, and zwitterionic polymers, packaging agents such as silicones, which may or may not be volatile or modified, film-forming agents, fatty substances including ceramides and fatty alcohols, preserving agents and opacifiers.

The compositions disclosed herein may also comprise at least one other additives, such as monoalcohols such as alkanols, polyols, anionic, cationic, nonionic, amphoteric, and zwitterionic surfactants, mineral thickeners, organic thickeners, such as anionic, cationic, nonionic, and amphoteric associative polymers.

Needless to say, a person skilled in the art will take care to select this or these optional additional compounds such that the advantageous properties intrinsically associated with the dye composition disclosed herein are not, or are not substantially, adversely affected by the addition or additions envisaged.

The pH of the dye composition as disclosed herein may generally range from 3 to 12, such as from 5 to 11. It may be adjusted to the desired value using acidifying or basifying agents usually used in the dyeing of keratin fibers, or alternatively using standard buffer systems.

Acidifying agents may be chosen from one or more of, for example, mineral acids and organic acids such as hydrochloric acid, orthophosphoric acid, sulphuric acid, carboxylic acids such as acetic acid, tartaric acid, citric acid, and lactic acid, and sulphonic acids.

Basifying agents may be chosen from one of more of, for example, aqueous ammonia, alkaline carbonates, alkanolamines such as mono-, di- and triethanolamine and derivatives thereof, sodium hydroxide, potassium hydroxide and the compounds of formula (XVI) below:

in which K is a propylene residue that is optionally substituted with at least one of hydroxyl groups and $C_1$–$C_4$ alkyl radicals; R36, R37, R38, and R39, which may be identical or different, are chosen from hydrogen atoms, $C_1$–$C_4$ alkyl radicals, and $C_1$–$C_4$ hydroxyalkyl radicals.

The dye composition disclosed herein may be in various forms, such as in the form of liquids, creams, and gels, or in any other form that is suitable for dyeing human keratin fibers, such as human hair.

Another embodiment disclosed herein is a process of direct dyeing, which comprises the application of a dye composition comprising a dye of formula (I) as defined above to human keratin fibers. After a leave-in time, the fibers are rinsed, revealing colored fibers.

The dye composition comprising the dye of formula (I) may be applied to the fibers in the presence of at least one oxidizing agent, which may cause bleaching of the fibre, i.e., lightening direct dyeing. The at least one oxidizing agent may be added to the composition comprising the polycationic direct dye at the time of use or it may be added directly onto the fiber.

Another embodiment disclosed herein is a process of oxidation dyeing, which comprises the application to the human keratin fibers of a dye composition comprising a dye of formula (I), at least one oxidation base and optionally at least one coupler, in the presence of at least one oxidizing agent.

The at least one oxidation base, the at least one coupler and the at least one oxidizing agent are as defined above.

The color may be revealed at acidic, neutral, and alkaline pH and the at least one oxidizing agent may be added to the composition at the time of use, or it may be introduced using an oxidizing composition comprising it, applied to the fibers simultaneously with or sequentially to the dye composition.

In the case of oxidation dyeing or lightening direct dyeing, the dye composition is mixed, for example, at the time of use, with a composition comprising, in a medium suitable for dyeing, at least one oxidizing agent, this at least one oxidizing agent being present in an amount that is sufficient to develop a coloration. The mixture obtained may then be applied to the fibers. After a leave-in time ranging from 3 to 50 minutes, such as from 5 to 30 minutes, the fibers are rinsed, washed with shampoo, rinsed again, and then dried.

The oxidizing composition may also comprise various adjuvants conventionally used in compositions for dyeing the hair, and as defined above.

The pH of the oxidizing composition comprising the oxidizing agent may be such that, after mixing with the dye composition, the pH of the resulting composition applied to the keratin fibers may range from 3 to 12, such as from 5 to 11. It may be adjusted to the desired value by means of acidifying or basifying agents usually used in the dyeing of human keratin fibers, and as defined above.

Another embodiment disclosed herein is a multi-compartment device or "kit", for example a 2-compartment device, for dyeing keratin fibers, such as the hair, in which a first compartment comprises the dye composition of the invention and a second compartment comprises the oxidizing composition. This device may be equipped with a means for applying the desired mixture to the hair, such as the devices described in French Patent No. FR 2 586 913 in the name of the Assignee.

The examples that follow, of dye compositions, are intended to illustrate the invention without being limiting in nature.

EXAMPLE 1

The dye composition below was prepared:

| | | |
|---|---|---|
| [1,4-phenylenebis[methylene(dimethyliminio)-3,1-ethanediyl]]bis[2-({4-[(4-dimethylaminophenyl)(cyclohexa-2,5-dienylidene}-4-dimethylammonium)methylene]-phenyl}ethylamino)ethyl] tetrachloride | 1.13 g | |
| Benzyl alcohol | 4.0 g | |
| Polyethylene glycol 6 EO | 6.0 g | |
| Hydroxyethylcellulose | 0.7 g | |
| Alkylpolyglucoside as an aqueous solution comprising 60% A.M.* | 4.5 g A.M. | |
| Phosphate buffer q.s pH | 7 | |
| Demineralized water q.s | 100 g | |

*Active Material

The above composition was applied to locks of natural or permanent-waved grey hair containing 90% white hairs, and was left on the hair for 20 minutes. After rinsing with running water and drying, the hair was dyed in a violet shade.

EXAMPLE 2

The dye composition below was prepared:

| | |
|---|---|
| 1H-Benzo[ij]quinolizinium 9-[bis(2,3,6,7-tetrahydro-1H,5H-benzo[ij]quinolizin-9-yl)methylene]-2,3,5,6,7,9-hexahydrotetrachloride | 1.09 g |

| | | | |
|---|---|---|---|
| -continued | | | |
| Oleic acid diethanolamide | | | 3 g |
| Lauric acid | | | 1 g |
| Ethylene glycol monoethyl ether | | | 5 g |
| Hydroxyethylcellulose | | | 2 g |
| 2-Amino-2-methyl-1-propanol | q.s | pH | 9.5 |
| Demineralized water | q.s | | 100 g |

The above composition was applied to locks of natural or permanent-waved grey hair containing 90% white hairs, and was left on the hair for 30 minutes. After rinsing with running water and drying, the hair was dyed in an orange-yellow shade.

What is claimed is:

1. A dye composition for dyeing human keratin fibers comprising, in a medium suitable for dyeing, at least one direct polycationic dye of formula (I) below:

$$\text{Col-Z-Col} \qquad (I)$$

in which

Col, which may be identical or different, is a monocationic dye chosen from azo dyes, methine dyes, azomethine dyes, phenothiazine dyes, triarylmethane dyes, xanthene dyes, phenanthridine dyes, and phthalocyanin dyes; and Z is chosen from linear and branched, saturated and unsaturated C1–C20 hydrocarbon-based groups comprising at least one nitrogen atom and bearing at least two cationic charges.

2. The composition according to claim 1, wherein the human keratin fibers are hair.

3. The composition according to claim 1, wherein Z has the structure of formula (II):

$$-Z_1-Z_2-Z_3- \qquad (II)$$

in which $Z_1$ and $Z_3$, which may be identical or different, are chosen from heterocycles bearing at least one hetero atom chosen from nitrogen, oxygen, sulphur, and phosphorus; and $Z_2$ is a linear or branched hydrocarbon-based group containing from 0 to 10 carbon atoms.

4. The composition according to claim 3, wherein $Z_2$ is a linear or branched hydrocarbon-based group containing from 2 to 6 carbon atoms.

5. The composition according to claim 3, wherein the heterocycles are 5- to 8-membered.

6. The composition according to claim 3, wherein at least one of the radicals chosen from $Z_1$ and $Z_2$ is a heterocycle fused with a benzene nucleus.

7. The composition according to claim 3, wherein $Z_1$ and $Z_3$ each comprise a cationic charge.

8. The composition according to claim 3, wherein the heterocyclic group is chosen from pyrroles, imidazoles, isoimidazoles, pyrazoles, and pyridines.

9. The composition according to claim 1, wherein Z has the structure of formula (III)

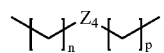

in which:

n represents an integer ranging from 1 to 10;

p represents an integer ranging from 1 to 10; and $Z_4$ represents a dicationic group containing from 2 to 16 carbon atoms, wherein the dicationic group is chosen from aliphatic, saturated or unsaturated, carbocyclic or polycarbocyclic, aromatic or polyaromatic, and heterocyclic or polyheterocyclic groups.

10. The composition according to claim 9, wherein n is an integer ranging from 2 to 5.

11. The composition according to claim 9, wherein p is an integer ranging from 2 to 5.

12. The composition according to claim 9, wherein $Z_4$ represents a dicationic group containing from 5 to 12 carbon atoms.

13. The composition according to claim 9, wherein the polycarbocyclic group is chosen from monocarbocyclic groups, dicarbocyclic groups, and tricarbocyclic groups.

14. The composition according to claim 9, wherein the polyaromatic group is chosen from monoaromatic groups, biaromatic groups, and triaromatic groups.

15. The composition according to claim 9, wherein the hetercyclic group comprises from 1 to 5 hetero atoms chosen from nitrogen, sulphur, oxygen, and phosphorus, and further wherein the heterocyclic group is optionally substituted with at least one group chosen from hydroxyls, carboxyls, $C_1$–$C_4$ alkoxycarbonyls, hydrogenocarbonyls, $C_1$–$C_4$ alkoxys, $C_1$–$C_4$ acyls, aminos, monoalkylaminos, dialkylaminos, $C_1$–$C_4$ monohydroxyalkyls, dihydroxyalkyls, cyanos, nitros, and sulphonatos.

16. The composition according to claim 9, wherein the group $Z_4$ is chosen from diazoniabicyclooctanes and bipyridines.

17. The composition according to claim 1, wherein Z is an aliphatic group.

18. The composition according to claim 9, wherein Z is an aliphatic group of formula (IV):

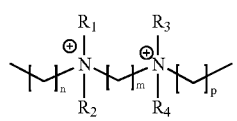

(IV)

in which n represents an integer ranging from 1 to 10;
m represents an integer ranging from 1 to 15;
p represents an integer ranging from 1 to 10; and
$R_1$, $R_2$, $R_3$, and $R_4$, which may be identical or different, are $C_1$–$C_6$ alkyl radicals.

19. The composition according to claim 18, wherein n represents an integer ranging from 2 to 5.

20. The composition according to claim 18, wherein m represents an integer ranging from 2 to 10.

21. The composition according to claim 18, wherein p represents an integer ranging from 2 to 5.

22. The composition according to claim 1, wherein the polycationic direct dye of formula (I) is chosen from:
N,N,N'',N''-tetramethyl-N,N''-bis{3-[4-[(3-methyl-2-(3H)-benzo-thiazolylidene)methyl]quinolinium-1-yl]butyl}-1,4-bipyridinium tetraiodide;
[1,4-phenylenebis[methylene(dimethyliminio)-3,1-ethanediyl]]bis[2-({4-[(4-dimethylaminophenyl)(cyclohexa-2,5-dienylidene}-4-dimethylammonium)-methylene]phenyl}ethylamino)ethyl];
[1,4-phenylenebis[methylene(diethyliminio)-3,1-ethanediyl]]bis[2-({4-[(4-dimethylaminophenyl)(cyclohexa-2,5-dienylidene]-4-dimethylammonium)methylene]phenyl}ethylamino)ethyl];
1,3'-Bipyridinium 1',1'''-[1,4-phenylenebis[methylene(dimethyliminio)-3,1-propanediyl]]bis[1',2'-dihydro-6'-hydroxy-4'-methyl-5'-[[4-(phenylazo)phenyl]azo] tetrachloride;
1,3'-Bipyridinium 1',1'''-[(2-hydroxy-1,3-propanediyl)bis[(dimethyliminio)-3,1-propanediyl]]bis[1',2'-dihydro-6'-hydroxy-4'-methyl-2'-oxo-5'-[[4-(phenylazo)phenyl]azo] tetrachloride;
N,N-bis{3-[4-[(3-methyl-2(3H)-benzothiazolylidene)methyl]quinolinium-1-yl]propyl}-1,4-diazoniabicyclo[2,2,2]octane tetraiodide;
N,N-bis{3-[4-[(3-methyl-2(3H)-benzothiazolylidene)methyl]quinolinium-1-yl]butyl}-1,4-diazoniabicyclo[2,2,2]octane tetraiodide;
Thiazolo[4,5-b]pyridinium 2,2'-[1,3-propanediylbis[(dimethyliminio)-3,1-propanediyl-1(4H)-quinolinyl-4-ylidenemethylidyne]]bis[6-bromo-4-methyl] tetraiodide;
Oxazolo[4,5-b]pyridinium 2,2'-[1,3-propanediylbis[(dimethyliminio)-3,1-propanediyl-1(4H)-quinolinyl-4-ylidenemethylidyne]]bis[4-methyl] tetraiodide;
Quinolinium 1,1'-[1,6-hexanediylbis[(dimethyliminio)-4,1-butanediyl]]bis[4-[(3-methyl-2(3H)-benzothiazolylidene)methyl] tetraiodide;
Quinolinium 1,1'-[1,6-hexanediylbis[(dimethyliminio)-3,1-propanediyl]]bis[4-[(3-methyl-2(3H)-benzothiazolylidene)methyl] tetraiodide;
Quinolinium 1,1'-[1,3-propanediylbis[(dimethyliminio)-4,1-butanediyl]]bis[4-[(3-ethyl-2(3H)-benzothiazolylidene)methyl] tetraiodide;
Quinolinium 1,1'-[1,3-propanediylbis[(dimethyliminio)-3,1-propanediyl]]bis[4-[(3-ethyl-2(3H)-benzothiazolylidene)methyl] tetraiodide;
Quinolinium 1,1'-[1,3-propanediylbis[(dimethyliminio)-5,1-pentanediyl]]bis[4-[(3-methyl-2(3H)-benzothiazolylidene)methyl] tetraiodide;
Quinolinium 4-[(3-methyl-2(3H)-benzothiazolylidene)methyl]-1-[3-[dimethyl]3-[dimethyl[4-[4-[(3-methyl-2(3H)-benzothiazolylidene)methyl]quinolinio]butyl]ammonio]propyl]ammonio]propyl] tetraiodide;
Quinolinium 1,1'-[1,3-propanediylbis[(dimethyliminio)-2,1-ethanediyl]]bis[4-[(3-methyl-2(3H)-benzothiazolylidene)methyl] tetraiodide;
Benzothiazolium 2,2'-[1,3-propanediylbis[(dimethyliminio)-3,1-propanediyl-1(2H)-pyridinyl-2-ylidenemethylidyne]]bis[3-methyl] tetraiodide;
N,N,N'',N''-tetramethyl-N,N''-bis{3-[4-[(3-methyl-2(3H)-benzothiazolylidene)methyl]quinolinium-1-yl]butyl}-1,3-propanediammonium tetraiodide;
Naphtho[1,2-d]thiazolium 2,2'-[1,3-propanediylbis[(dimethyliminio)-3,1-propanediyl-1(4H)-quinolinyl-4-ylidenemethylidyne]]bis[1-methyl] tetraiodide;
8H-Naphth[2',1':4,5]oxazolo[3,2-a]azepinium 12,12'-[methylenebis[-(dimethyliminio)-3,1-propanediyl-1(4H)-quinolinyl-4-ylidene-2,1-ethanediylidene]]bis[9,10,11,12-tetrahydro-9-[3-(trimethylammonio)propyl];
Naphth[2',1':4,5]oxazolo[3,2-a]pyridinium 11,11'-[methylenebis[(dimethyliminio)-3,1-propanediyl-1(4H)-quinolinyl-4-ylidene-2,1-ethanediylidene]]bis[8,9,10,11-tetrahydro-8-[3-(trimethylammonio)propyl];
Naphth[2,1-d]oxazolium 2,2'-[methylenebis[(dimethyliminio)-3,1-propanediyl-1(4H)-quinolinyl-4-ylidene-1-propen-1-yl-3-ylidene]]bis[3-[3-(trimethylammonio)propyl];

8H-Naphtho[2',1':4,5]thiazolo[3,2-a]azepinium 12,12'-[methylenebis[(dimethyliminio)-3,1-propanediyl-1(4H)-quinolinyl-4-ylidene-2,1-ethanediylidene]]bis[9,10,11,12-tetrahydro-9-[3-(trimethylammonio)propyl];

Naphtho[2',1':4,5]thiazolo[3,2-a]pyridinium 11, 11'-[methylenebis[(dimethyliminio)-3,1-propanediyl-1(4H)-quinolinyl-4-ylidene-2,1-ethanediylidene]]bis[8,9,10,11-tetrahydro-8-[3-(trimethylammonio)propyl];

Naphtho[2,1-d]thiazolium 2,2'-[methylenebis[(dimethyliminio)-3,1-propanediyl-1(4H)-quinolinyl-4-ylidene-1-propen-1-yl-3-ylidene]]bis[3-[3-(trimethylammonio)propyl];

Naphth[2',1':4,5]oxazolo[3,2-a]azocinium 13,13'-[methylenebis-[(dimethyliminio)-3,1-propanediyl-1(4H)-quinolinyl-4-ylidene-2,1-ethanediylidene]]bis[8,9,10,11,12,13-hexahydro];

Naphth[2',1':4,5]oxazolo[3,2-a]pyridinium 11,11'-[methylenebis-[(dimethyliminio)-3,1-propanediyl-1(4H)-quinolinyl-4-ylidene-2,1-ethanediylidene]]bis[8,9,10,11-tetrahydro];

8H-Naphtho[2,1-d]pyrrolo[2,1-b]oxazolium 10,10'-[methylenebis-[(dimethyliminio)-3,1-propanediyl-1(4H)-quinolinyl-4-ylidene-2,1-ethanediylidene]]bis[9,10-dihydro];

Naphtho[2',1':4,5]thiazolo[3,2-a]azocinium 13,13'-[methylenebis-[(dimethyliminio)-3,1-propanediyl-1(4H)-quinolinyl-4-ylidene-2,1-ethanediylidene]]bis[8,9,10,11,12,13-hexahydro];

Naphtho[2',1':4,5]thiazolo[3,2-a]pyridinium 11,11'-[methylenebis-[(dimethyliminio)-3,1-propanediyl-1(4H)-quinolinyl-4-ylidene-2,1-ethanediylidene]]bis[8,9,10,11-tetrahydro];

8H-Naphtho[2,1-d]pyrrolo[2,1-b]thiazolium 10,10'-[methylenebis[(dimethyliminio)-3,1-propanediyl-1(4H)-quinolinyl-4-ylidene-2,1-ethanediylidene]]bis[9,10-dihydro];

Benzoxazolium 2,2'-[1,3-propanediylbis[(dimethyliminio)-3,1-propanediyl-1(4H)-pyridinyl-4-ylidenemethylidyne]]bis[3-methyl] tetraiodide;

Benzothiazolium 2,2'-[1,3-propanediylbis[(dimethyliminio)-3,1-propanediyl-1(4H)-pyridinyl-4-ylidene-1-propenyl-3-ylidene]]bis[3-methyl] tetraiodide;

Quinolinium 1,1'-[1,3-propanediylbis[(dimethyliminio)-3,1-propanediyl]]bis[4-[3-(3-methyl-2(3H)-benzothiazolylidene)-1-propenyl] tetraiodide;

Benzothiazolium 2,2'-[1,3-propanediylbis[(dimethyliminio)-3,1-propanediyl-1(4H)-pyridinyl-4-ylidenemethylidyne]]bis[3-methyl] tetraiodide;

Benzoxazolium 2,2'-[1,3-propanediylbis[(dimethyliminio)-2,1-ethanediyl-1(4H)-quinolinyl-4-ylidene-1-propen-1-yl-3-ylidene]]bis[3-methyl] tetraiodide;

Quinolinium 1,1'-[1,3-propanediylbis[(dimethyliminio)-3,1-propanediyl]]bis[4-[3-(3-methyl-2(3H)-benzoxazolylidene)-1-propenyl] tetraiodide;

Phenanthridinium 5,5'-[1,2-ethanediylbis[(dimethyliminio)-3,1-propanediyl]]bis[3,8-diamino-6-phenyl] tetraiodide;

Dimethylenebis[2-({4-[(4-dimethylaminophenyl)(cyclohexa-2,5-dienylidene}-4-dimethylammonium)methylene]phenyl}ethylamino)-ethyl]dimethylammonium; and Tetramethylenebis[2-({4-[(4-dimethylaminophenyl)(cyclohexa-2,5-dienylidene}-4-dimethylammonium)methylene]phenyl}ethylamino)-ethyl]dimethylammonium.

23. The composition according to claim 1, wherein the at least one direct polycationic dye of formula (I) is present in a concentration ranging from 0.001% to 5% by weight relative to the total weight of the dye composition.

24. The composition according to claim 23, wherein the at least one direct polycationic dye of formula (I) is present in a concentration ranging from 0.05% to 2% by weight relative to the total weight of the dye composition.

25. The composition according to claim 1, further comprising at least one cosmetic adjuvant chosen from monoalcohols; polyols; anionic, cationic, nonionic, amphoteric, and zwitterionic surfactants, and mixtures thereof; mineral thickeners, organic thickeners; and anionic, cationic, nonionic, and amphoteric associative polymers.

26. The composition according to claim 25, wherein the adjuvants are present in an amount for each of them ranging from 0.01% to 20% by weight relative to the total weight of the dye composition.

27. The composition according to claim 1, further comprising at least one direct dye other than those of formula (I), chosen from neutral, acidic, and cationic nitrobenzene direct dyes; neutral, acidic, and cationic azo direct dyes; neutral, acidic, and cationic quinone, anthraquinone direct dyes; azine direct dyes; methine direct dyes; triarylmethane direct dyes; indoamine direct dyes; and natural direct dyes.

28. The composition according to claim 1, further comprising at least one oxidizing agent.

29. The composition according to claim 28, wherein the at least one oxidizing agent is hydrogen peroxide.

30. The composition according to claim 1, further comprising at least one oxidation base.

31. The composition according to claim 30, wherein the at least one oxidation base is chosen from para-phenylenediamines, bis(phenyl)alkylenediamines, para-aminophenols, ortho-aminophenols, heterocyclic bases, and the acid addition salts thereof.

32. The composition according to claim 30, further comprising at least one coupler.

33. The composition according to claim 32, wherein the at least one coupler is chosen from meta-phenylenediamines, meta-aminophenols, meta-diphenols, naphthalene-based couplers, heterocyclic couplers, and the acid addition salts thereof.

34. A process for direct dyeing of human keratin fibers comprising applying to the fibers at least one dye composition comprising, in a medium suitable for dyeing, at least one direct polycationic dye of formula (I) below:

$$Col-Z-Col \qquad (I)$$

in which

Col, which may be identical or different, is a monocationic dye chosen from azo dyes, methine dyes, azomethine dyes, phenothiazine dyes, triarylmethane dyes, xanthene dyes, phenanthridine dyes, and phthalocyanin dyes; and Z is chosen from linear and branched, saturated and unsaturated $C_1$–$C_{20}$ hydrocarbon-based groups comprising at least one nitrogen atom and bearing at least two cationic charges.

35. The process according to claim 34, wherein the human keratin fibers are hair.

36. The process according to claim 34, wherein dye composition further comprises at least one oxidizing agent.

37. The process according to claim 36, wherein the at least one oxidizing agent is mixed with the at least one dye composition at the time of use.

38. The process according to claim 36, wherein the at least one oxidizing agent is applied to the fibers in the form of an oxidizing composition, simultaneously with or sequentially to the at least one dye composition.

39. A process for the oxidation dyeing of human keratin fibers, comprising applying to the fibers:
- (a) at least one dye composition in a medium suitable for dyeing, comprising at least one direct polycationic dye of formula (I) below:

Col-Z-Col  (I)

in which
    Col, which may be identical or different, is a monocationic dye chosen from azo dyes, methine dyes, azomethine dyes, phenothiazine dyes, triarylmethane dyes, xanthene dyes, phenanthridine dyes, and phthalocyanin dyes; and
    Z is chosen from linear and branched, saturated and unsaturated C1–C20 hydrocarbon-based groups comprising at least one nitrogen atom and bearing at least two cationic charges;
- (b) at least one oxidation base; and
- (c) optionally at least one coupler in the presence of at least one oxidizing agent.

40. The process according to claim 39, wherein the human keratin fibers are hair.

41. The process according to claim 39, wherein the at least one oxidizing agent is mixed with the at least one dye composition at the time of use.

42. The process according to claim 39, wherein the at least one oxidizing agent is applied to the keratin fibers in the form of an oxidizing composition, simultaneously with or sequentially to the at least one dye composition.

43. A two-compartment device, or "kit", for dyeing human keratin fibres, wherein a first compartment comprises a dye composition comprising, in a medium suitable for dyeing, at least one direct polycationic dye of formula (I) below:

Col-Z-Col  (I)

in which
Col, which may be identical or different, is a monocationic dye chosen from azo dyes, methine dyes, azomethine dyes, phenothiazine dyes, triarylmethane dyes, xanthene dyes, phenanthridine dyes, and phthalocyanin dyes; and
Z is chosen from linear and branched, saturated and unsaturated C1–C20 hydrocarbon-based groups comprising at least one nitrogen atom and bearing at least two cationic charges, and
a second compartment comprises at least one oxidizing composition.

44. The kit according to claim 43, wherein the human keratin fibers are hair.

* * * * *